(12) United States Patent
Woznica et al.

(10) Patent No.: US 6,642,178 B2
(45) Date of Patent: Nov. 4, 2003

(54) ADJUVANT BLEND FOR ENHANCING EFFICACY OF PESTICIDES

(75) Inventors: Zenon J. Woznica, Fargo, ND (US); Calvin Messersmith, Fargo, ND (US); John Nalewaja, Fargo, ND (US)

(73) Assignee: North Dakota State University, Fargo, ND (US)

( * ) Notice: Subject to any disclaimer, the term of this patent is extended or adjusted under 35 U.S.C. 154(b) by 0 days.

(21) Appl. No.: 09/992,475

(22) Filed: Nov. 14, 2001

(65) Prior Publication Data

US 2003/0125211 A1 Jul. 3, 2003

(51) Int. Cl.$^7$ .............................. C05G 3/02; C05G 3/06; C05C 1/00; C05C 11/00; A01N 25/30
(52) U.S. Cl. ..................... 504/211; 504/234; 504/235; 504/253; 504/343; 504/363; 71/54; 71/59; 71/61
(58) Field of Search ................. 71/54, 59, 61; 504/363, 211, 253, 235, 234, 343

(56) References Cited

U.S. PATENT DOCUMENTS

| | | | |
|---|---|---|---|
| 4,017,641 A | 4/1977 | DiGiulio | 424/365 |
| 4,092,273 A | 5/1978 | Inamorato et al. | 252/548 |
| 4,125,398 A | 11/1978 | Roth | 71/115 |
| 4,227,911 A | 10/1980 | Leonard et al. | 71/77 |
| 4,749,404 A | 6/1988 | Parsons | 71/92 |
| 4,954,279 A | 9/1990 | Ma et al. | 252/70 |
| 4,971,630 A | 11/1990 | Skaptason | 71/117 |
| 5,078,782 A | 1/1992 | Nielsen et al. | 71/100 |
| 5,118,338 A | 6/1992 | Moller | 71/86 |
| 5,266,553 A | 11/1993 | Champion et al. | 504/206 |
| 5,341,932 A | 8/1994 | Chen et al. | 206/524.7 |
| 5,346,704 A | 9/1994 | Lajoie | 424/717 |
| 5,356,861 A | 10/1994 | Gednalski et al. | 504/206 |
| 5,407,899 A | 4/1995 | Howell | 504/152 |
| 5,409,885 A | 4/1995 | Derian et al. | 504/116 |
| 5,411,932 A | 5/1995 | Yoshida et al. | 504/132 |
| 5,430,005 A | 7/1995 | Kassebaum et al. | 504/206 |
| 5,468,715 A | 11/1995 | Joseph et al. | 504/101 |
| 5,563,112 A | 10/1996 | Barnes, III | 504/125 |
| 5,658,855 A | 8/1997 | Nalewaja et al. | 504/214 |
| 5,871,666 A | 2/1999 | Gross | 252/312 |
| 5,919,733 A | 7/1999 | Sedun et al. | 504/320 |
| RE37,313 E | 8/2001 | Roberts | 424/405 |

OTHER PUBLICATIONS

Green et al., "Surfactant Structure and Concentration Strongly Affect Rimsulfuron Activity", Weed Technology, vol. 7, pp. 633–640, 1993.
Holloway, "Adjuvants for Foliage–Applied Agrochemicals: The Need for More Science not Serendipity?" 4$^{th}$ International Symposium on Adjuvants for Agrochemicals, Melbourne, Australia, pp. 167–175, Oct. 3–6, 1995.
"Imazaquin–Imazethapyr", WISSA Handbook, 7$^{th}$ Ed., pp. 166, 1994.
Miller et al., "Barban–Aqueous Nitrogen Combinations for Wild Oat(*Avena fatua*) Control", Weed Science, vol. 26, Issue 4, pp. 344–348, Jul. 1978.
Nalewaja et al., "Salts and Surfactants Influence Nicosulfuron Activity", Weed Technology, vol. 9, pp. 587–593, 1995.
Nalewaja et al., Spray Carrier Salts Affect Herbicide Toxicity to Kochia (*Kochia scoparia*), Weed Technology, vol. 7, pp. 154–158, 1993.
"Nicosulfuron", WSSA Herbicide Handbook, 7$^{th}$ Ed., pp. 216–217, 1994.
North Dakota State University Weed Control Research entitled, "Summary of 2000 Weed Control Experiments", 2000.
"Picloram–Primisulfuron", WSSA Herbicide Handbook, 7$^{th}$ Ed., 1994.
Renegade Specimen Label and Material Safety Data Sheet, Feb. 2000.
Wanamarta et al., "Overcoming Antagonistic Effects of Na–Bentazon on Sethoxydim Absorption", Weed Technology, vol. 7, pp. 322–325, 1993.

*Primary Examiner*—S. Mark Clardy
(74) *Attorney, Agent, or Firm*—Fitch, Even, Tabin & Flannery

(57) ABSTRACT

The present invention relates to a homogenous adjuvant blend for use in spray carriers containing herbicides. The homogenous adjuvant blend includes a nitrogen fertilizer, a pH adjuster, modified vegetable oil, and a blend of nonionic surfactants having high, intermediate, and low hydrophilic-lipophilic balance (HLB).

53 Claims, No Drawings

ADJUVANT BLEND FOR ENHANCING EFFICACY OF PESTICIDES

This invention relates to a homogenous adjuvant blend for use in spray carriers containing herbicides, which are used to control weeds or other undesired vegetation. More specifically, the homogenous adjuvant blend of the invention includes a neutral blend of nitrogen fertilizer, a pH adjuster, modified vegetable oil, and a blend of nonionic surfactants having high, intermediate, and low hydrophilic-lipophilic balance (HLB).

BACKGROUND

Herbicides used in controlling weeds or undesired vegetation in agriculture may be applied by postemergence spraying of a herbicide on the crop. The spray carrier for the herbicide is usually a water-based adjuvant mixture containing an effective amount of known herbicide. Adjuvants are commonly added to herbicidal spray mixtures to enhance postemergence weed control and/or to reduce spray drift during herbicide applications.

Postemergence weed control applications are enhanced when the spray containing the herbicide is retained on the weed surface. To obtain sufficient retention of the herbicide on the weed surface, many "sticker" compositions or agents, including methylated vegetable oils or mineral based oils and surface active agents (surfactants), are used as adjuvants. These adjuvants act to improve adherence of the herbicide on weeds, help retain droplets of the spray solution on the plant, and improve penetration of the herbicide into the plant.

In addition to spray retention by the weed, other additives in the form of liquid nitrogen based fertilizer solutions have been found, for example, to enhance the control of wild oats by herbicides such as barban. Miller et al., *Weed Science*, 1978, Vol. 4, pp. 344–348. Recently surfactants have been combined with liquid fertilizers (usually 28% nitrogen, comprising a mixture of about 50% ammonium nitrate and about 50% urea). The results however are variable depending on surfactants used and nitrogen fertilizer employed. It was found that certain salts and surfactants influence nicosulfuron herbicide activity. Nalewaja et al., *Weed Technology*, 1995, Vol. 9, pp. 587–593.

Some acidic additives have previously been used which are designed to lower pH and enhance the acidity of the spray carrier water formulation, which was believed to both benefit herbicide adsorption and also to prevent alkaline hydrolysis of certain insecticides. Acids and buffering agents are sometimes also used to reduce antagonism from alkaline salts found in the spray carrier water.

It has been noted that adjuvants differ greatly in herbicide enhancement depending on the specific surfactant and the herbicide used. In some cases, adjuvant can result in decreased performance. Halloway, *4th International Symposium on Adjuvants for Agrochemicals*, 1995, FR. & Bulletin, No. 193.

Adjuvants which are a three component system including an alkaline amine pH regulator, a non-ionic surfactant, and a neutral ammonium salt, such as ammonium nitrate, ammonium chloride, and ammonium sulfate, are described in U.S. Pat. No. 5,658,855. All three components were required to provide the desired phytotoxicity.

One concern over the use of adjuvants is not only in its ability to enhance herbicide efficacy but in its ability to maintain product stability. Many adjuvants may be blended with herbicides and water that are available at the site of blending. In some cases, the available blending water may contain minerals or other substances that result in formation of precipitates and general instability of the composition.

SUMMARY

The present invention relates to homogenous adjuvant blends for use in a spray carrier of postemergence herbicides applied as an aqueous spray solution to areas infested with undesired weeds or plants to control the same. The adjuvant compositions of the present invention are stable and act synergistically at low rates to increase spray retention, prevent pesticide antagonism from salts in spray water, and provide lipophilic and hydrophilic environments in the spray deposits that enhance leaf penetration and efficacy of herbicides. The adjuvant of the present invention is provided as a single stable formulation that reduces the need to add separate components to a spray tank mix.

The adjuvant of the present invention is a multi-component composition that includes a neutral blend of nitrogen fertilizers, modified vegetable oil, a pH adjuster which is the base for adjusting the pH to the alkaline range, and a blend of high, intermediate, and low hydrophilic-lipophilic balance (HLB) nonionic surfactants.

Nitrogen fertilizers include nitrogen fertilizers such as ammonium nitrate, urea, ammonium chloride, ammonium nitrate-urea fertilizer solutions, ammonium sulfate, and mixtures thereof. In an important aspect of the invention, the nitrogen fertilizer ranges from about 30 to about 45 percent by weight of the concentrate adjuvant composition. The preferred nitrogen fertilizer is ammonium nitrate-urea fertilizer where the percent of nitrogen is about 2 percent to about 34 percent, preferably about 28 percent.

The second component of the homogenous adjuvant blend of the present invention is a pH adjuster. The pH adjuster of the invention is effective for providing an alkaline pH of above about 7 up to about 10 for the final spray solution that is applied to the plants. The pH adjuster may be organic and/or inorganic. Examples of of pH adjusters include triethanolamine, primary amino alcohols, ammonium hydroxide and mixtures thereof. In an important aspect of the invention, the pH adjuster component is about 0.1 weight percent to about 20 weight percent of the adjuvant composition, preferably about 10 percent by weight of the adjuvant composition.

The third component of the homogenous adjuvant blend is modified vegetable oil. The modified vegetable oil may be selected from a group including methylated, ethylated, and butylated seed oils from all major crops. In an important aspect of the invention, the preferred modified vegetable oil is methylated canola oil. The modified vegetable oil of the composition is about 5 weight percent to about 80 weight percent by weight of the adjuvant composition, and preferably is about 20 percent by weight of the adjuvant composition.

The next components of the homogenous adjuvant blend are two nonionic surfactants. In an important aspect of the invention, the nonionic surfactants are block copolymers. One of the block copolymer surfactants has a high HLB above about 14 and the other nonionic block copolymer surfactant has a HLB of 10 or less. In an important aspect, the high HLB nonionic surfactant has a HLB of above about 14 to about 18. The low HLB nonionic surfactant has a HLB of above about 1 to about 10. Each block copolymer surfactant component is about 1 to about 20 weight percent of the adjuvant composition, preferably about 1 to about 10 weight percent of the adjuvant composition, and more preferably is about 6 percent by weight of the adjuvant composition. Block copolymers useful in the present invention include copolymers of propylene oxide and ethylene oxide.

The adjuvant composition further includes at least two intermediate HLB nonionic surfactants. The intermediate nonionic surfactant may be a nonionic secondary alcohol ethoxylate surfactant having intermediate HLB values above about 10 to about 14. Each secondary alcohol ethoxylate surfactant is about 3 to about 33 weight percent of the adjuvant composition.

In another aspect, about 1 percent of the homogenous adjuvant blend of the present invention is blended with water and with an effective amount of herbicide to provide a postemergence herbicidal spray composition, which is applied for weed control purposes. In this aspect of the invention, the herbicidal spray composition includes about 95 to 99 percent water, about 0.001 to about 4 percent herbicide, and about 1 percent of the adjuvant of the present invention, based on the weight of the herbicidal spray composition. The herbicide is customarily added to the water at the recommended label amount; for example, herbicide in an amount from about 0.1 to about 4 ounces per acre of the herbicide active ingredients is a typical application rate.

DETAILED DESCRIPTION

The homogenous adjuvant blend of the present invention is a multi-component mixture including a neutral nitrogen fertilizer, pH adjuster, modified vegetable oil, two high molecular weight nonionic block copolymer surfactants (average molecular weight between 1,000 and 10,000), and two nonionic secondary alcohol ethoxylate surfactants. The percentage of each ingredient is blended to provide a homogenous and stable formulation. As used herein a "homogenous and stable" formulation means that all components of the adjuvant composition when mixed together form a clear, continuous blend that does not separate during storage at temperatures between 32° F. and 122° F. for at least about 180 days.

In an important aspect of the invention, the homogenous adjuvant blend increases the efficacy of certain herbicides. The ingredients, acting synergistically, produce a low application rate formulation. In practice, similar ingredients are added to the spray mixture separately, at much higher rates. Using the adjuvant blend components in one spray formulation, at a rate of about 1% of the spray mixture volume, provides a convenient and time-saving combination for farmers. The present invention increases spray retention, prevents pesticide antagonism from salts in the spray water, and enhances leaf penetration by providing a lipophilic and hydrophilic environment.

Nitrogen Fertilizer

In an important aspect of the invention, the nitrogen fertilizer ranges from about 30 to about 45 percent by weight of the adjuvant concentrate composition. Nitrogen fertilizers include nitrogen fertilizers such as ammonium nitrate, urea, ammonium chloride, ammonium nitrate-urea fertilizer solutions, ammonium sulfate, and mixtures thereof. The preferred nitrogen fertilizer is ammonium nitrate-urea fertilizer where the percent of nitrogen is about 2 percent to about 34 percent, preferably about 28 percent. Ammonium nitrate-urea liquid fertilizer is preferred because: 1) it is effective for increasing efficacy of many postemergence herbicides when it is applied together with oils and surfactants; and 2) in comparison to the other nitrogen fertilizers, it is the most compatible compound when in a blend with modified vegetable oil, pH adjuster, and nonionic surfactants.

pH Adjuster

In an important aspect of the invention, the pH adjuster of the invention provides an alkaline pH of the final spray solution of above about 7 up to about 10, which is effective to increase solubility of the herbicide active ingredient. This is particularly important when used with herbicides from the sulfonylurea group (e.g., foramsulfuron, nicosulfuron, rimulfuron, primisulfuron).

Alkaline compounds are especially important in the present invention. Examples of pH adjusters include ammonium hydroxide, triethanolamine, primary amino alcohols (e.g., 2-amino-1-butanol, 2-amino-2-methyl-1-propanol, 2-amino-2-methyl-1,3-propanediol, 2-amino-2-methyl-1-propanol, 2-dimethylamino-2-methyl-1-propanol, 2-amino-2-ethyl-1,3-propanediol, tris(hydroxymethyl)aminomethane, 2-dimethylamino-2-methyl-1-propanol), and mixtures thereof. The pH adjuster component should be about 0.1 to about 20 percent by weight of the adjuvant composition, and in an important aspect preferably is an organic pH adjuster at about 10 percent by weight of the adjuvant composition.

Modified Vegetable Oil

The adjuvant composition of the present invention includes modified vegetable oil from about 5 to about 80 percent by weight of the adjuvant composition, preferably about 20 percent by weight of the adjuvant composition. The modified vegetable oil is especially important in the present invention and may be selected from a group including methylated, ethylated, and butylated seed oils from all major crops. Modified methylated, ethylated, and butylated vegetable oils in general increase efficacy of many herbicides more than petroleum or non-modified vegetable oils. Modified vegetable oils mainly increase the herbicide penetration and are especially effective with many herbicides when they are applied in mixtures with nitrogen fertilizers (e.g., with liquid ammonium nitrate-urea fertilizer).

Nonionic Block Copolymer Surfactants

In an important aspect of the invention, the adjuvant composition includes two nonionic block copolymer surfactants, the first having a high HLB (Hydrophilic-Lipophilic Balance) broadly above about 14 to about 18, while the other has a low HLB broadly above 1 to about 10. Each block copolymer surfactant is about 1 to about 20 percent by weight of the adjuvant composition, and preferably each block copolymer surfactant is about 6 percent by weight of the adjuvant composition.

High HLB indicates that a surfactant molecule is relatively more water than oil soluble. One system of obtaining HLB is by dividing the percentage of the water soluble portion of the surfactant molecule by 5. HLB values for surfactants are usually provided by the surfactant supplier and are also available from McCutcheon's Emulsifiers & Detergents, McCutcheon Division, McCutcheon Publishing Co., 175 Rock Road, Glen Rock, N.J. 07452. High HLBs of the present invention are considered hydrophilic. In an important aspect of the invention, certain water soluble herbicides are enhanced more by high than low HLB surfactants.

Examples of suitable block copolymer surfactants having a high HLB are Pluronics, block copolymers of propylene oxide and ethylene oxide, products of BASF Corp., (L64, HLB 15; L84, HLB 14; P85, HLB 16, P104, HLB 13; P105, HLB 15). Examples of suitable non-ionic surfactants having a low HLB are Pluronics, block copolymers of propylene oxide and ethylene oxide, products of BASF Corp., (L62, HLB 7; L92, HLB 6; P123, HLB 8).

Nonionic Secondary Ethoxylate Alcohol Surfactants

In another aspect of the invention, the adjuvant composition include at least two additional nonionic surfactants. The additional nonionic surfactants may be secondary alcohol ethoxylate surfactants having a HLB of above about 10 to about 14. In this aspect of the invention, the adjuvant composition includes additional nonionic surfactants in about 3 to about 33 weight percent by weight of the adjuvant composition.

In an important aspect of this invention, the secondary alcohol ethoxylate surfactants, in addition to the two block copolymer surfactants, are effective for providing enhanced adjuvant stability for a storage time of from 1 to 180 days at a temperature range between 32° F. and 122° F.

Examples of suitable secondary alcohol ethoxylate surfactants having an intermediate HLB are Tergitols, (15-S-5, HLB 10.5; 15-S-9, HLB 13.3), products of Union Carbide, Corp.

Application of Homogenous Adjuvant Blend

The homogenous adjuvant blend is customarily formulated and sold in two and one half (2½) gallon or larger containers. The adjuvant blend is used to make up the spray mixture, which also includes spray water (about 95% to about 99%) and a herbicidally effective amount of a postemergence herbicide, customarily 2% or less by weight of the aqueous spray mixture. The herbicide is customarily added to the water at the recommended label amount; for example, in an amount effective for providing an application rate of from about 0.1 to about 4 ounces per acre of the herbicide active ingredient. In this aspect of the invention, the spray applied to the plants is typically from about 0.5 to 2 weight percent adjuvant, preferably 1 weight percent, from about 0.001 to about 4 weight percent, preferably about 0.001 to about 2 weight percent herbicide, with the remainder of the spray being water.

The adjuvant blend of the present invention is effective for use with herbicides that require addition of oil based adjuvants, nitrogen fertilizers or surfactants and for which solubility in water is increased by high pH, which includes sulfonylurea and weak acid herbicides. The modified vegetable oil, surfactants and nitrogen fertilizer of the present invention act to improve spray retention and herbicide absorption by weeds and the high pH maintains the herbicide in a more available chemical form for absorption.

Preferably, the herbicides employed in this invention are selected from the group consisting of:

Nicosulfuron (sold under the tradename Accent) which is the compound [[[[(4,6-dimethoxy-2-pyrimidinyl) amino]carbonyl] amino]sulfonyl-N,N-dimethyl-3-pyridine carboxy amide;

Rimsulfuron (sold under the trade name Matrix)which is the compound N-[[(4,6-dimethoxy-2-pyrimidinyl) amino]carbonyl]-3-(ethylsulfonyl)-2-pyridinesulfonamide);

Imazethapyr (sold under the trade name Pursuit), 2-[4,5-dihydro-4-methyl-4-(1-methylethyl)-5-oxo-1H-imidaz ol-2-yl]-5-ethyl-3-pyridinecarboxylic acid;

Primisulfuron (sold under the trade name Beacon), 2-[[[[[4,6-bis(difluoromethoxy)-2-pyrimidinyl]amino]carbonyl]amino]sulfonyl]benzoic acid;

Foramsulfuron,2-[[[[(4,6-dimethoxy-2-pyrimidinyl)amino]carbonyl]amino]sulfonyl]-4-(formylamino)-N,N-dimeth ylbenzamide;

Mesotrione, (sold under the trade name Callisto), 2-[4-(methylsulfonyl)-2-nitrobenzoyl-1,3-cyclohexanedione;

Quizalofop, (sold under the trade name Assure II), 2-[4-[(6-chloro-2-quinoxalinyl)oxy]phenoxy]propanoic acid;

Clethodim, (sold under the trade name Select), (E,E)-2-[1-[[(3-chloro-2-propenyl)oxy]imino]propyl]-5-[2-(ethylthio)propyl]-3-hyroxy-2-cyclohexen-1-on;

Flucarbazone (sold under the trade name Everest), 4,5-dihydro-3-methoxy-4-methyl-5-oxo-N-[[2-(trifluoromethoxy)phen Atrazine (sold under various trade names), 6-chloro-N-ethyl-N'-(1-methylethyl)-1,3,5-triazine-2,4-diamine, and mixtures thereof.

In an important aspect, the invention provides postemergence herbicidal aqueous spray compositions that include:

(A) a nitrogen fertilizer in an amount of from about 30 to about 45 percent by weight of the adjuvant blend;

(B) a pH adjuster in an amount effective for providing an alkaline pH of above about 7 to about 10 of the final herbicidal aqueous spray mixture;

(C) a modified vegetable oil;

(D) a high hydrophilic-lipophilic balance (HLB) nonionic surfactant having a HLB of above about 14;

(E) at least two intermediate nonionic sufactants having a HLB of about 10 to about 14;

(F) a low HLB nonionic surfactant having a HLB of about 10 or less;

(G) a herbicide; and (H) additional water to make up the final spray solution.

EXAMPLES

The example homogenous adjuvant blend named as L-64.11.2.1 (TABLE 1) can be prepared as follows. Methylated canola oil (20 parts), Pluronic L 92.RTM (6 parts), Pluronic L 64.RTM (6 parts), Tergitol 15-S-5.RTM (8 parts), Tergitol 15-S-9.RTM (16 parts), and triethanolamine (10 parts) are pre-stirred until the mixture is homogenous; however, it still remains cloudy. Next the 28% N ammonium nitrate-urea fertilizer (34 parts) is added gradually, while slowly stirring, until the formulation is homogenous, clear, without separation. The formulation was stable for a storage time of from 1 to at least 180 days at temperature ranges between 32° F. and 122° F.

TABLE 1

Components of example homogenous adjuvant blend composition L-64.11.2.1.

| Component | Percent weight of final formulation | Function |
| --- | --- | --- |
| Methylated canola oil | 20.0 | Increase herbicide activity. |
| Pluronic L 92.RTM, HLB 6.0 | 6.0 | Increase herbicide activity; compatibility agent. |
| Pluronic L 64.RTM, HLB 15.0 | 6.0 | Increase herbicide activity; compatibility agent. |
| Tergitol 15-S-5.RTM, HLB 10.5 | 8.0 | Increase herbicide activity; formulation compatibility agent. |
| Tergitol 15-S-9.RTM, HLB 13.3 | 16.0 | Increase herbicide activity; formulation compatibility agent |

TABLE 1-continued

Components of example homogenous adjuvant blend composition L-64.11.2.1.

| Component | Percent weight of final formulation | Function |
|---|---|---|
| Triethanolamine | 10.0 | Stabilize final herbicidal spray mixture pH at above about 7 to about 10. |
| 28% N liquid ammonium nitrate-urea fertilizer | 34.0 | Prevent antagonism from spray carrier salts; increase herbicide activity. |
| TOTAL | 100.0 | |

Pluronic L 64.RTM and Pluronic L 92.RTM block copolymer nonionic surfactants, both from BASF Corp.; Tergitol 15-S-5.RTM and Tergitol 15-S-9.RTM secondary alcohol ethoxylate surfactants, both from Union Carbide Corp.

The adjuvants Scoil.RTM, Quad 7.RTM, 28% N liquid fertilizer, and L-64.11.2.1 were added to water (volume per volume at concentration shown in Table 2) with nicosulfuron (0.2 oz/A) to prepare the final aqueous spray mixture applied at 8.5 gal/A on 3–4 leaf stage large crabgrass. TABLE 2 includes the results of assessment made 3 WAT (weeks after treatment). Visible injury rating is on a scale 0 to 100% with 0% representing no visible injury and 100% complete kill.

Nonionic surfactant Activator 90.RTM plus 28% N liquid fertilizer and methylated seed oil Scoil.RTM plus 28% N liquid fertilizer (as tank mixes) were much more effective in enhancing nicosulfuron efficacy than nonionic surfactant and methylated seed oil applied without 28% N. However, the homogenous, multicomponent adjuvant of present invention L-64.11.2.1 provided the highest nicosulfuron efficacy.

TABLE 2

Large crabgrass control 3 WAT with nicosulfuron (0.2 oz/A) as influenced by adjuvants (greenhouse tests).

| Adjuvant | % visible injury | % fresh weight reduction |
|---|---|---|
| None | 31 | 57 |
| Activator 90.RTM 0.5% | 39 | 64 |
| Activator 90.RTM 0.5% + 28% N 2% | 53 | 74 |
| Scoil.RTM 0.5% | 50 | 70 |
| Scoil.RTM 0.5% + 28% N 2% | 78 | 85 |
| Scoil.RTM 1% | 70 | 76 |
| Scoil.RTM 1% + 28% N 2% | 86 | 93 |
| Quad 7.RTM 1% | 90 | 88 |
| L-64.2.1 0.5% | 94 | 89 |
| L-64.2.1 0.75% | 97 | 90 |
| L-64.2.1 1% | 95 | 92 |
| LSD (0.05) | 4 | 5 |

Activator 90.RTM is a nonionic surfactant of alkylpolyoxyethylene ethers and free fatty acids from Loveland Industries; Scoil.RTM is methylated vegetable oil from AGSCO Inc.; Quad 7.RTM is basic blend adjuvant from AGSCO Inc.; 28% N is liquid ammonium nitrate-urea fertilizer with 28% nitrogen; L-64.11.2.1 is an experimental homogenous adjuvant which refers to the present invention consisting of methylated canola oil (20%), triethanolamine (10%), mixture of Pluronic L 64.RTM and Pluronic L 92.RTM block copolymer nonionic surfactants (6%+6%), both from BASF Corp., mixture of Tergitol 15-S-5.RTM and Tergitol 15-S-9.RTM secondary alcohol ethoxylate surfactants (8%+16%), both from Union Carbide Corp., and ammonium nitrate-urea liquid nitrogen (28% N) fertilizer (34%).

The adjuvants Scoil.RTM, Quad 7.RTM, 28% N liquid fertilizer, and L-64.11.2.1 were added to water (volume per volume at concentration shown in TABLE 3) with nicosulfuron (0.04 oz/A) to prepare the final aqueous spray mixture applied at 8.5 gal/A on 3-leaf stage green foxtail. TABLE 3 includes the results of assessment made 2 WAT (weeks after treatment).

Homogenous, multicomponent adjuvant of present invention L-64.11.2.1 applied at concentration of 1% provided equal nicosulfuron efficacy as methylated seed oil Scoil.RTM at 2% plus 28% N liquid fertilizer at 4%.

TABLE 3

Green foxtail control 2 WAT with nicosulfuron (0.04 oz/A) as influenced by adjuvants (greenhouse tests).

| Adjuvant | % fresh weight reduction |
|---|---|
| None | 0 |
| Scoil.RTM 0.5% | 45 |
| Scoil.RTM 1% | 72 |
| Scoil.RTM 2% | 76 |
| Scoil.RTM 2% + 28% N 4% | 82 |
| Quad 7.RTM 1% | 85 |
| L-64.11.2.1 1% | 84 |
| LSD (0.05) | 10 |

Scoil.RTM is methylated vegetable oil from AGSCO Inc.; Quad 7.RTM is a basic blend adjuvant from AGSCO Inc.; 28% N is liquid ammonium nitrate-urea fertilizer with 28% nitrogen; L-64.11.2.1 is an experimental homogenous adjuvant, which refers to the present invention consisting of methylated canola oil (20%), triethanolamine (10%), mixture of Pluronic L 64.RTM and Pluronic L 92.RTM block copolymer nonionic surfactants (6%+6%), both from BASF Corp., mixture of Tergitol 15-S-5.RTM and Tergitol 15-S-9.RTM secondary alcohol ethoxylate surfactants (8%+16%), both from Union Carbide Corp., and ammonium nitrate-urea liquid nitrogen (28% N)fertilizer (34%).

The results of three field tests on volunteer oat and wheat control are shown in TABLES 4, 5, and 6.

The adjuvants Activator 90.RTM, Scoil.RTM, Prime Oil.RTM, Quad 7.RTM, and L-64.11.2.1 were added to water (volume per volume at concentration or ate per acre shown in TABLES 4, 5, and 6) with clethodim (0.25 oz/A), imazethapyr (0.25 oz/A) or quizalofop (0.25 oz/A) to prepare the final aqueous spray mixture applied at 8.5 gal/A to 3–4-leaf stage wheat and oat. TABLES 4, 5, and 6 include the results of assessment made 2 and 6 WAT (weeks after treatment).

Homogenous, multicomponent adjuvant of present invention L-64.11.2.1 applied at concentration of 1% provided consistently equal or higher clethodim, imazethapyr, and quizalofop efficacy than the reference commercial adjuvants applied at recommended rates.

TABLE 4

Volunteer wheat and oat control 2 and 6 WAT with
clethodim at 0.25 oz/A as influenced by adjuvants,
Fargo, ND, field experiment, 2001.

|  | 07/12 | | 08/03 | |
| --- | --- | --- | --- | --- |
| Adjuvant | Oat | Wheat | Oat | Wheat |
| Activator 90.RTM 0.5% | 38 | 53 | 25 | 30 |
| Scoil.RTM 1% | 86 | 86 | 86 | 90 |
| Scoil.RTM 1.5 pt/A | 86 | 85 | 89 | 96 |
| Prime Oil.RTM 2 pt/A | 84 | 84 | 85 | 90 |
| Quad 7.RTM 1% | 83 | 81 | 78 | 85 |
| L-64.11.2.1 1% | 93 | 93 | 93 | 96 |
| L-64.11.2.1 1% | 94 | 94 | 94 | 96 |
| LSD (0.05) | 7 | 6 | 14 | 12 |

Activator 90.RTM is a nonionic surfacant of alkylpolyoxyethylene ethers and free fatty acids from Loveland Industries. Scoil.RTM is methylated vegetable oil from AGSCO Inc.; Prime Oil.RTM is petroleum oil from Agriliance; Quad 7.RTM is a basic blend adjuvant from AGSCO Inc.; L-64.11.2.1 is an experimental homogenous adjuvant, which refers to present invention consisting of methylated canola oil (20%), triethanolamine (10%), mixture of Pluronic L 64.RTM and Pluronic L 92.RTM block copolymer nonionic surfactants (6%+6%), both from BASF Corp., mixture of Tergitol 15-S-5.RTM and Tergitol 15-S-9.RTM secondary alcohol ethoxylate surfactants (8%+16%), both from Union Carbide Corp., and ammonium nitrate-urea liquid nitrogen (28% N) fertilizer (34%).

TABLE 5

Volunteer wheat and oat control 2 and 6 WAT with
imazethapyr at 0.25 oz/A as influenced by adjuvants,
Fargo, ND, field experiment, 2001.

|  | 07/12 | | 08/03 | |
| --- | --- | --- | --- | --- |
| Adjuvant | Oat | Wheat | Oat | Wheat |
| Activator 90.RTM 0.5% | 75 | 78 | 74 | 81 |
| Scoil.RTM 1% | 80 | 88 | 85 | 94 |
| Scoil.RTM 1.5 pt/A | 85 | 89 | 93 | 95 |
| Prime Oil.RTM 2 pt/A | 79 | 85 | 75 | 91 |
| Quad 7.RTM 1% | 80 | 84 | 79 | 94 |
| L-64.11.2.1 1% | 81 | 85 | 85 | 93 |
| L-64.11.2.1 1% | 88 | 90 | 91 | 95 |
| LSD (0.05) | 7 | 7 | 11 | 8 |

Activator 90.RTM is a nonionic surfacant of alkylpolyoxyethylene ethers and free fatty acids from Loveland Industries. Scoil.RTM is methylated vegetable oil from AGSCO Inc.; Prime Oil.RTM is petroleum oil from Agriliance; Quad 7.RTM is a basic blend adjuvant from AGSCO Inc.; L-64.11.2.1 is an experimental homogenous adjuvant, which refers to present invention consisting of methylated canola oil (20%), triethanolamine (10%), mixture of Pluronic L 64.RTM and Pluronic L 92.RTM block copolymer nonionic surfactants (6%+6%), both from BASF Corp., mixture of Tergitol 15-S-5.RTM and Tergitol 15-S-9.RTM secondary alcohol ethoxylate surfactants (8%+16%), both from Union Carbide Corp., and ammonium nitrate-urea liquid nitrogen (28% N) fertilizer (34%).

TABLE 6

Volunteer wheat and oat control 2 WAT with quizalofop at
0.25 oz/A as influenced by adjuvants, Fargo, ND, field
experiment, 2001.

|  | 07/12 | |
| --- | --- | --- |
| Adjuvant | Oat | Wheat |
| Activator 90.RTM 0.5% | 77 | 86 |
| Scoil.RTM 1% | 81 | 91 |
| Scoil.RTM 1.5 pt/A | 80 | 91 |
| Prime Oil.RTM 2 pt/A | 84 | 94 |
| Quad 7.RTM 1% | 93 | 96 |
| L-64.11.2.1 1% | 93 | 98 |
| L-64.11.2.1 1% | 95 | 97 |
| LSD (0.05) | 9 | 6 |

Activator 90.RTM is a nonionic surfacant of alkylpolyoxyethylene ethers and free fatty acids from Loveland Industries. Scoil.RTM is methylated vegetable oil from AGSCO Inc.; Prime Oil.RTM is petroleum oil from Agriliance; Quad 7.RTM is a basic blend adjuvant from AGSCO Inc.; L-64.11.2.1 is an experimental homogenous adjuvant, which refers to present invention consisting of methylated canola oil (20%), triethanolamine (10%), mixture of Pluronic L 64.RTM and Pluronic L 92.RTM block copolymer nonionic surfactants (6%+6%), both from BASF Corp., mixture of Tergitol 15-S-5.RTM and Tergitol 15-S-9.RTM secondary alcohol ethoxylate surfactants (8%+16%), both from Union Carbide Corp., and ammonium nitrate-urea liquid nitrogen (28% N) fertilizer (34%).

The results of a field test on weed control with foramsulfuron in corn are shown in TABLE 7. The adjuvants Scoil.RTM, Quad 7.RTM, and L-64.11.2.1 were added to water (at concentration shown in TABLE 7) with the foramsulfuron (0.75 and 1.25 oz/A) to prepare the final aqueous spray mixture applied at 8.5 gal/A.

Homogenous, multicomponent adjuvant of present invention L-64.11.2.1 applied at 1% concentration was equally or more effective than the reference commercial adjuvants Scoil.RTM or Quad 7.RTM applied at 1% concentration of total spray volume and without any visible corn injury.

TABLE 7

Yellow foxtail and common cocklebur control 3 WAT with
foramsulfuron at 0.75 and 1.25 oz/A in corn as influenced by
adjuvants, Casselton, ND, 2000.

|  |  | 06/27 | | |
| --- | --- | --- | --- | --- |
| Adjuvant | Foramsulfuron Oz/A | Corn Injury | Yellow foxtail | Common cocklebur |
| Scoil.RTM 1% | 0.75 | 0 | 80 | 78 |
| Quad 7.RTM 1% | 0.75 | 0 | 83 | 80 |
| L-64.11.2.1 1% | 0.75 | 0 | 85 | 84 |
| Scoil.RTM 1% | 1.25 | 0 | 88 | 76 |
| Quad 7.RTM 1% | 1.25 | 0 | 88 | 86 |
| L-64.11.2.1 1% | 1.25 | 0 | 89 | 91 |
| LSD (0.05) |  | NS | 8 | 6 |

Scoil.RTM is methylated vegetable oil from AGSCO Inc.; Quad 7.RTM is a basic blend adjuvant from AGSCO Inc.; L-64.11.2.1 is an experimental homogenous adjuvant, which refers to present invention consisting of methylated canola oil (20%), triethanolamine (10%), mixture of Pluronic L 64.RTM and Pluronic L 92.RTM block copolymer nonionic surfactants (6%+6%), both from BASF Corp., mixture of Tergitol 15-S-5.RTM and Tergitol 15-S-9.RTM secondary alcohol ethoxylate surfactants (8%+16%), both from Union Carbide Corp., and ammonium nitrate-urea liquid nitrogen (28% N) fertilizer (34%).

The results of a field test on weed control with nicosulfuron plus rimsulfuron (Steadfast.RTM) in corn are shown in TABLE 8. The adjuvants Activator 90.RTM, Scoil.RTM, Quad 7.RTM, and L-64.11.2.1 were added to water (at concentration shown in TABLE 8) with nicosulfuron plus rimsulfuron (0.2+0.1 oz active ingredient/A) to prepare the final aqueous spray mixture applied at 8.5 gal/A.

Homogenous, multicomponent adjuvant of present invention L-64.11.2.1 applied at 1% concentration and at 1.5 pt/A was equally or more effective than the reference commercial adjuvants Activator 90.RTM, Scoil.RTM, Quad 7.RTM, and Prime Oil.RTM and without any visible corn injury.

TABLE 8

Yellow foxtail and common cocklebur control 3 WAT with nicosulfuron plus rimsulfuron at 0.2 + 0.1 oz/A in corn as influenced by adjuvants, Casselton, ND, 2001.

| | 06/27 | | |
|---|---|---|---|
| Adjuvant | Corn Injury | Yellow foxtail | Common cocklebur |
| Activator 90.RTM 0.5% | 0 | 65 | 41 |
| Scoil.RTM 1% | 0 | 69 | 64 |
| Scoil.RTM 1.5 pt/A | 0 | 81 | 74 |
| Prime Oil.RTM 2 pt/A | 0 | 70 | 49 |
| Quad 7.RTM 1% | 0 | 78 | 53 |
| L-64.11.2.1 1% | 0 | 83 | 79 |
| L-64.11.2.1 1.5 pt/A | 0 | 89 | 79 |
| LSD (0.05) | NS | 10 | 17 |

Activator 90.RTM is a nonionic surfactant of alkylpolyoxyethylene ethers and free fatty acids from Loveland Industries. Scoil.RTM is methylated vegetable oil from AGSCO Inc.; Prime Oil.RTM is petroleum oil from Agriliance; Quad 7.RTM is basic blend adjuvant from AGSCO Inc.; L-64.11.2.1 is an experimental homogenous adjuvant, which refers to present invention consisting of methylated canola oil (20%), triethanolamine (10%), mixture of Pluronic L 64.RTM and Pluronic L 92.RTM block copolymer nonionic surfactants (6%+6%), both from BASF Corp., mixture of Tergitol 15-S-5.TRM and Tergitol 15-S-9.TRM secondary alcohol ethoxylate surfactants (8%+16%), both from Union Carbide Corp., and ammonium nitrate-urea liquid nitrogen (28% N) fertilizer (34%).

The results of a field test on weed control with nicosulfuron plus rimsulfuron plus clopyralid plus flumetsulam (Accent Gold.RTM) in corn are shown in TABLE 9. The adjuvants Activator 90.RTM, Scoil.RTM, Prime Oil.RTM, Quad 7.RTM, and L-64.11.2.1 were added to water (at concentration shown in TABLE 9) with nicosulfuron plus rimsulfuron plus clopyralid plus flumetsulam (0.1+0.1+0.9+0.3 oz active ingredient/A) to prepare the final aqueous spray mixture applied at 8.5 gal/A.

Homogenous, multicomponent adjuvant of present invention L-64.11.2.1 applied at 1% concentration and at 1.5 pt/A was equally or more effective than the reference commercial adjuvants, Activator 90.RTM, Scoil.RTM, Quad 7.RTM, and Prime Oil.RTM and without enhancing corn injury.

TABLE 9

Yellow foxtail and common cocklebur control 4 WAT with nicosulfuron plus rimsulfuron plus clopyralid plus flumetsulam at 0.1 + 0.1 + 0.9 + 0.3 oz/A in corn as influenced by adjuvants, Oakes, ND, 2001.

| | 07/17 | | |
|---|---|---|---|
| Adjuvant | Corn Injury | Yellow foxtail | Common lambsquarters |
| Activator 90.RTM 0.5% | 6 | 66 | 60 |
| Scoil.RTM 1% | 7 | 80 | 81 |
| Scoil.RTM 1.5 pt/A | 10 | 90 | 89 |
| Prime Oil.RTM 2 pt/A | 9 | 84 | 86 |
| Quad 7.RTM 1% | 9 | 90 | 93 |
| L-64.11.2.1 1% | 10 | 93 | 90 |
| L-64.11.2.1 1.5 pt/A | 9 | 95 | 95 |
| LSD (0.05) | NS | 11 | 9 |

Activator 90.RTM is a nonionic surfactant of alkylpolyoxyethylene ethers and free fatty acids from Loveland Industries. Scoil.RTM is methylated vegetable oil from AGSCO Inc.; Prime Oil.RTM is petroleum oil from Agriliance; Quad 7.RTM is basic blend adjuvant from AGSCO Inc.; L-64.11.2.1 is an experimental homogenous adjuvant, which refers to present invention consisting of methylated canola oil (20%), triethanolamine (10%), mixture of Pluronic L 64.RTM and Pluronic L 92.RTM block copolymer nonionic surfactants (6%+6%), both from BASF Corp., mixture of Tergitol 15-S-5.RTM and Tergitol 15-S-9.RTM secondary alcohol ethoxylate surfactants (8%+16%), both from Union Carbide Corp., and ammonium nitrate-urea liquid nitrogen (28% N) fertilizer (34%).

The results of a field test on weed control with nicosulfuron plus rimsulfuron plus atrazine (Basis Gold.RTM) in corn are shown in TABLE 10. The adjuvants Activator 90.RTM, Scoil.RTM, Prime Oil.RTM, Quad 7.RTM, and L-64.11.2.1 were added to water (at concentration shown in TABLE 10) with nicosulfuron plus rimsulfuron plus atrazine (0.1+0.1+7.6 oz active ingredient/A) to prepare the final aqueous spray mixture applied at 8.5 gal/A.

Homogenous, multicomponent adjuvant of present invention L-64.11.2.1 applied at 1% concentration and at 1.5 pt/A was equally or more effective than the reference commercial adjuvants Activator 90.RTM, Scoil.RTM, Quad 7.RTM, and Prime Oil.RTM and without any visible corn injury.

TABLE 10

Yellow foxtail, common lambquarters, volunteer flax, and wheat control 6 WAT with nicosulfuron plus rimsulfuron plus atrazine at 0.1 + 0.1 + 7.6 oz/A in corn as influenced by adjuvants, Oakes, ND, 2001.

| | 08/31 | | | | |
|---|---|---|---|---|---|
| Adjuvant | Corn Injury | Yellow foxtail | Common lambs-quarter | Flax | Wheat |
| Activator 90.RTM 0.5% | 0 | 63 | 90 | 59 | 68 |
| Scoil.RTM 1% | 0 | 79 | 97 | 75 | 74 |
| Scoil.RTM 1.5 pt/A | 0 | 81 | 99 | 78 | 80 |
| Prime Oil.RTM 2 pt/A | 0 | 75 | 99 | 76 | 75 |
| Quad 7.RTM 1% | 0 | 58 | 90 | 68 | 75 |
| L-64.11.2.1 1% | 0 | 83 | 96 | 78 | 78 |
| L-64.11.2.1 1.5 pt/A | 0 | 86 | 97 | 84 | 84 |
| LSD (0.05) | NS | 12 | 6 | 9 | 10 |

Activator 90.RTM is a nonionic surfactant of alkylpolyoxyethylene ethers and free fatty acids from Loveland Industries. Scoil.RTM is methylated vegetable oil from AGSCO Inc.; Prime Oil.RTM is petroleum oil from Agriliance; Quad 7 is basic blend adjuvant from AGSCO Inc.; L-64.11.2.1 is an experimental homogenous adjuvant, which refers to present invention consisting of methylated canola oil (20%), triethanolamine (10%), mixture of Pluronic L 64.RTM and Pluronic L 92.RTM block copolymer nonionic surfactants (6%+6%), both from BASF Corp., mixture of Tergitol 15-S-5.RTM and Tergitol 15-S-9.RTM secondary alcohol ethoxylate surfactants (8%+16%), both from Union Carbide Corp., and ammonium nitrate-urea liquid nitrogen (28% N) fertilizer (34%).

Numerous modifications and variations in practice of the invention are expected to occur to those skilled in the art upon consideration of the foregoing detailed description of the invention. Consequently, such modifications and variations are intended to be included within the scope of the following claims.

What is claimed is:

1. A homogeneous and stable adjuvant blend comprising
   a nitrogen fertilizer in an amount of from about 30 to about 45 percent by weight of the blend;
   a pH adjuster in an amount effective for providing an alkaline pH of above about 7 to about 10 when in a final spray composition;
   a modified vegetable oil; from about 1 to about 20 weight percent of a high hydrophilic-lipophilic balance (HLB) nonionic surfactant having a HLB of above about 14;
   from about 3 to about 33 weight percent of at least two intermediate HLB nonionic surfactants having a HLB of above about 10 to about 14; and
   from about 1 to about 20 weight percent of a low HLB nonionic surfactant having a HLB of about 10 or less.

2. An adjuvant blend according to claim 1 wherein the nitrogen fertilizer is selected from the group consisting of ammonium nitrate, urea, ammonium chloride, ammonium nitrate-urea, ammonium sulfate and mixtures thereof.

3. An adjuvant blend according to claim 1 wherein the pH adjuster is selected from the group consisting of ammonium hydroxide, triethanolamine, primary amino alcohols, and mixtures thereof.

4. An adjuvant blend according to claim 1 wherein the modified vegetable oil is selected from the group consisting of methylated, ethylated and butylated seed oils.

5. An adjuvant blend according to claim 4 wherein the adjuvant blend contains from about 5 to about 80 weight percent modified vegetable oil, based on the weight of the adjuvant blend.

6. An adjuvant blend according to claim 1 wherein the high HLB nonionic surfactant has a HLB of above about 14 to about 18.

7. An adjuvant blend according to claim 1 wherein the low HLB nonionic surfactant has a HLB of above about 1 to about 10.

8. An adjuvant blend according to claim 1 wherein the high and low nonionic surfactants are block copolymers.

9. An adjuvant blend according to claim 8 wherein the block copolymers are selected from the group consisting of copolymers of propylene oxide and ethylene oxide.

10. A homogenous and stable adjuvant blend for use in herbicidal spray compositions comprising:
    a nitrogen fertilizer in an amount from about 30 to about 45 percent by weight of the adjuvant blend, wherein the nitrogen fertilizer is selected from the group consisting of ammonium nitrate, urea, ammonium chloride, ammonium nitrate-urea, ammonium sulfate and mixtures thereof;
    a pH adjuster in an amount effective for providing an alkaline pH of above about 7 to about 10 in the final herbicidal spray composition, wherein the pH adjuster is selected from the group consisting of ammonium hydroxide, triethanolamine, primary amino alcohols, and mixtures thereof;
    a modified vegetable oil selected from the group consisting of methylated, ethylated and butylated seed oils;
    from about 1 to about 20 weight percent of a high hydrophilic-lipophilic balance (HLB) block copolymer nonionic surfactant having a HLB of above about 14;
    from about 3 to about 33 weight percent of at least two intermediate HLB nonionic surfactants having a HLB of above about 10 to about 14; and
    from about 1 to about 20 weight percent of a low HLB block copolymer nonionic surfactant having a HLB of about 10 or less.

11. A homogenous adjuvant blend according to claim 10 wherein the adjuvant blend contains from about 5 to about 80 weight percent modified vegetable oil, based on the weight of the adjuvant blend.

12. A homogenous adjuvant blend according to claim 10 wherein the high HLB nonionic surfactant has a HLB of above about 14 to about 18.

13. A homogenous adjuvant blend according to claim 10 wherein the low HLB nonionic surfactant has a HLB of above about 1 to about 10.

14. A homogenous adjuvant blend according to claim 10 wherein the block copolymers are selected from the group consisting of copolymers of propylene oxide and ethylene oxide.

15. A homogenous and stable adjuvant blend comprising
    a nitrogen fertilizer in an amount from about 30 to about 45 percent by weight of the blend;
    a pH adjuster in an amount effective for providing an alkaline pH of above about 7 to about 10 when in a final spray composition;
    a modified vegetable oil;
    from about 1 to about 20 weight percent of a high hydrophilic-lipophilic balance (HLB) nonionic surfactant having a HLB of above about 14;
    from about 3 to about 33 weight percent of a low HLB nonionic surfactant having a HLB of about 10 or less; and
    from about 1 to about 20 weight percent of at least two intermediate HLB nonionic surfactants.

16. A homogenous adjuvant blend according to claim 15 wherein the nitrogen fertilizer is selected from the group consisting of ammonium nitrate, urea, ammonium chloride, ammonium nitrate-urea, ammonium sulfate and mixtures thereof.

17. A homogenous adjuvant blend according to claim 15 wherein the pH adjuster is selected from the group consisting of ammonium hydroxide, triethanolamine, primary amino alcohols, and mixtures thereof.

18. A homogenous adjuvant blend according to claim 15 wherein the modified vegetable oil is selected from the group consisting of methylated, ethylated and butylated seed oils.

19. A homogenous adjuvant blend according to claim 18 wherein the adjuvant blend contains from about 5 to about 80 weight percent modified vegetable oil, based on the weight of the adjuvant blend.

20. A homogenous adjuvant blend according to claim 15 wherein the high HLB nonionic surfactant has a HLB of above about 14 to about 18.

21. A homogenous adjuvant blend according to claim 15 wherein the low HLB nonionic surfactant has a HLB of above about 1 to about 10.

22. A homogenous adjuvant blend according to claim 15 wherein the intermediate HLB nonionic surfactant has a HLB of above about 10 to about 14.

23. A homogenous adjuvant blend according to claim 15 wherein the high and low nonionic surfactants are block copolymers.

24. A homogenous adjuvant blend according to claim 23 wherein the block copolymers are selected from the group consisting of copolymers of propylene oxide and ethylene oxide.

25. A method of controlling weeds which comprises applying a postemergence herbicidal spray composition to weeds and/or other undesired vegetation, the herbicidal spray composition comprising a stable and homogeneous adjuvant blend, an effective amount of a postemergence herbicide, and additional water to make up the final spray composition, the adjuvant blend comprising:
  a nitrogen fertilizer in an amount from about 30 to about 45 percent by weight of the adjuvant blend;
  a pH adjuster in an amount effective for providing an alkaline pH of above about 7 to about 10 when in the spray composition;
  a modified vegetable oil;
  from about 1 to about 20 weight percent of a high hydrophilic-lipophilic balance (HLB) nonionic surfactant having a HLB of above about 14;
  from about 3 to about 33 weight percent of at least two intermediate HLB nonionic surfactants having a HLB of above about 10 to about 14; and
  from about 1 to about 20 weight percent of a low HLB nonionic surfactant having a HLB of about 10 or less.

26. A method of controlling weeds according to claim 25 wherein the nitrogen fertilizer is selected from the group consisting of ammonium nitrate, urea, ammonium chloride, ammonium nitrate-urea, ammonium sulfate and mixtures thereof.

27. A method of controlling weeds according to claim 25 wherein the pH adjuster is selected from the group consisting of ammonium hydroxide, triethanolamine, primary amino alcohols, and mixtures thereof.

28. A method of controlling weeds according to claim 25 wherein the modified vegetable oil is selected from the group consisting of methylated, ethylated and butylated seed oils.

29. A method of controlling weeds according to claim 25 wherein the adjuvant blend contains from about 5 to about 80 weight percent modified vegetable oil, based on the weight of the adjuvant blend.

30. A method of controlling weeds according to claim 25 wherein the high HLB nonionic surfactant has a HLB of above about 14 to about 18.

31. A method of controlling weeds according to claim 25 wherein the low HLB nonionic surfactant has a HLB of above about 1 to about 10.

32. A method of controlling weeds according to claim 25 wherein the high and low nonionic surfactants are block copolymers.

33. A method of controlling weeds according to claim 32 wherein the block copolymers are selected from the group consisting of copolymers of propylene oxide and ethylene oxide.

34. A method of controlling weeds according to claim 25 wherein the herbicide is selected from the group consisting of nicosulfuron, foramsulfuron, primisulfuron, mesosulfuron, mesotrione, rimsulfuron, imazethapyr, flucarbazone, quizalofop, clethodim, atrazine and mixtures thereof.

35. A method of controlling weeds according to claim 25 wherein the herbicidal spray composition includes from about 0.001 to about 4 weight percent herbicide, based on the weight of the herbicidal spray composition.

36. A postemergence herbicidal aqueous spray composition comprising a stable and homogeneous adjuvant blend, an effective amount of a herbicide, and additional water to make up the final spray composition, the adjuvant blend comprising:
  a nitrogen fertilizer in an amount of from about 30 to about 45 percent by weight of the adjuvant blend;
  a pH adjuster in an amount effective for providing an alkaline pH of above about 7 to about 10 when in the spray composition;
  a modified vegetable oil;
  from about 1 to about 20 weight percent of a high hydrophilic-lipophilic balance (HLB) nonionic surfactant having a HLB of above about 14;
  from about 3 to about 33 weight percent of a low HLB nonionic surfactant having a HLB of about 10 or less; and
  from about 1 to about 20 weight percent of at least two intermediate HLB nonionic surfactants having a HLB of above about 10 to about 14.

37. A postemergence herbicidal aqueous spray composition according to claim 36 wherein the nitrogen fertilizer is selected from the group consisting of ammonium nitrate, urea, ammonium chloride, ammonium nitrate-urea, ammonium sulfate and mixtures thereof.

38. A postemergence herbicidal aqueous spray composition according to claim 36 wherein the pH adjuster is selected from the group consisting of ammonium hydroxide, triethanolamine, primary amino alcohols, and mixtures thereof.

39. A postemergence herbicidal aqueous spray composition according to claim 36 wherein the modified vegetable oil is selected from the group consisting of methylated, ethylated and butylated seed oils.

40. A postemergence herbicidal aqueous spray composition according to claim 36 wherein the adjuvant blend contains from about 5 to about 80 weight percent modified vegetable oil, based on the weight of the adjuvant blend.

41. A postemergence herbicidal aqueous spray composition according to claim 36 wherein the high HLB nonionic surfactant has a HLB of above about 14 to about 18.

42. A postemergence herbicidal aqueous spray composition according to claim 36 wherein the low HLB nonionic surfactant has a HLB of above about 1 to about 10.

43. A postemergence herbicidal aqueous spray composition according to claim 36 wherein the high and low nonionic surfactants are block copolymers.

44. A postemergence herbicidal aqueous spray composition according to claim 43 wherein the block copolymers are selected from the group consisting of copolymers of propylene oxide and ethylene oxide.

45. A postemergence herbicidal aqueous spray composition according to claim 36 wherein the herbicide is selected from the group consisting of nicosulfuron, foramsulfuron, primisulfuron, mesosulfuron, mesotrione, rimsulfuron, imazethapyr, flucarbazone, quizalofop, clethodim, atrazine and mixtures thereof.

46. A homogeneous and stable adjuvant blend comprising:

a nitrogen fertilizer in an amount of from about 30 to about 45 percent by weight of the blend, the nitrogen fertilizer selected from the group consisting of urea, ammonium nitrate urea, and mixtures thereof;

a pH adjuster in an amount effective for providing an alkaline pH of above about 7 to about 10 when in a final spray composition;

a modified vegetable oil;

from about 1 to about 20 weight percent of a high hydrophilic-lipophilic balance (HLB) nonionic surfactant having a HLB of above about 14;

from about 3 to about 33 weight percent of at least two intermediate HLB nonionic surfactants having a HLB of above about 10 to about 14; and from about 1 to about 20 weight percent of a low HLB nonionic surfactant having a HLB of about 10 or less.

47. An adjuvant blend according to claim 46 wherein the ph adjuster is selected from the group consisting of ammonium hydroxide, triethanolamine, primary amino alcohols, and mixtures thereof.

48. An adjuvant blend according to claim 46 wherein the modified vegetable oil is selected from the group consisting of methylated, ethylated and butylated seed oils.

49. An adjuvant blend according to claim 46 wherein the adjuvant blend contains from about 5 to about 80 weight percent modified vegetable oil, based on the weight of the adjuvant blend.

50. An adjuvant blend according to claim 46 wherein the high HLB nonionic surfactant has a HLB of above about 14 to about 18.

51. An adjuvant blend according to claim 46 wherein the low HLB nonionic surfactant has a HLB of above about 1 to about 10.

52. An adjuvant blend according to claim 46 wherein the high and low nonionic surfactants are block copolymers.

53. An adjuvant blend according to claim 46 wherein the block copolymers are selected from the group consisting of copolymers of propylene oxide and ethylene oxide.

* * * * *

UNITED STATES PATENT AND TRADEMARK OFFICE
CERTIFICATE OF CORRECTION

PATENT NO. : 6,642,178 B2
DATED : November 4, 2003
INVENTOR(S) : Woznica et al.

It is certified that error appears in the above-identified patent and that said Letters Patent is hereby corrected as shown below:

Column 13,
Line 19, after "comprising" insert -- : --.
Line 26, after "oil;" begin new paragraph.

Column 15,
Line 17, after "comprising" insert -- : --.

Signed and Sealed this

Sixth Day of July, 2004

JON W. DUDAS
*Acting Director of the United States Patent and Trademark Office*